United States Patent
Yao

(10) Patent No.: US 11,185,484 B2
(45) Date of Patent: Nov. 30, 2021

(54) SOLID ANHYDROUS COMPOSITION FOR CARING FOR AND/OR MAKING UP KERATIN MATERIALS

(71) Applicant: L'OREAL, Paris (FR)

(72) Inventor: Chunlei Yao, Shanghai (CN)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/649,865

(22) PCT Filed: Dec. 28, 2017

(86) PCT No.: PCT/CN2017/119378
§ 371 (c)(1),
(2) Date: Mar. 23, 2020

(87) PCT Pub. No.: WO2019/127211
PCT Pub. Date: Jul. 4, 2019

(65) Prior Publication Data
US 2020/0268627 A1    Aug. 27, 2020

(51) Int. Cl.
| | | |
|---|---|---|
| *A61K 8/37* | (2006.01) | |
| *A61K 8/02* | (2006.01) | |
| *A61K 8/92* | (2006.01) | |
| *A61Q 19/00* | (2006.01) | |

(52) U.S. Cl.
CPC ............ *A61K 8/375* (2013.01); *A61K 8/0216* (2013.01); *A61K 8/922* (2013.01); *A61Q 19/001* (2013.01); *A61K 2800/10* (2013.01); *A61K 2800/31* (2013.01); *A61K 2800/43* (2013.01)

(58) Field of Classification Search
None
See application file for complete search history.

(56) References Cited

U.S. PATENT DOCUMENTS

| | | | |
|---|---|---|---|
| 6,280,757 B1 * | 8/2001 | McAtee | A61K 8/0208 424/400 |
| 9,192,557 B2 | 11/2015 | Baars et al. | |
| 2013/0052246 A1 * | 2/2013 | Ito | A61Q 1/02 424/401 |
| 2016/0303031 A1 | 10/2016 | El Achkar et al. | |

FOREIGN PATENT DOCUMENTS

| | | | |
|---|---|---|---|
| WO | WO 2007/006536 A1 | 1/2007 | |
| WO | WO 2009/037201 A1 | 3/2009 | |
| WO | WO 2011/137938 A1 | 11/2011 | |
| WO | WO-2011137938 A1 * | 11/2011 | ............... A61Q 1/12 |
| WO | WO 2014/097134 A1 | 6/2014 | |
| WO | WO 2015/082369 A1 | 6/2015 | |
| WO | WO 2017/008243 A1 | 1/2017 | |

OTHER PUBLICATIONS

International Search Report and Written Opinion dated Oct. 8, 2018 in PCT/CN2017/119378 filed on Dec. 28, 2017.
Extended European Search Report dated Jul. 9, 2021 in European Patent Application No. 17936063.1, 9 pages.
Mintel, "Joystick," Database GNPD [Online], Database accession No. 4227191, XP055819096, Aug. 2016, 5 pages.
Mintel, "Lipstick," Database GNPD [Online], Database accession No. 3506387, XP055819101, Oct. 2015, 4 pages.
Mintel, "Healthy Glow Lip Balm," Database GNPD [Online], Database accession No. 2759427, XP055819103, Nov. 2014, 4 pages.
Mintel, "Crystal Shine Lips," Database GNPD [Online], Database accession No. 1846682, XP055819107, Aug. 2012, 4 pages.

* cited by examiner

*Primary Examiner* — Melissa S Mercier
(74) *Attorney, Agent, or Firm* — Oblon, McClelland, Maier & Neustadt, L.L.P.

(57) ABSTRACT

A solid anhydrous composition for caring for and/or making up keratin materials comprising: a) at least one triglyceride oil according to formula (I): $CH_2(OOCR_1)CH(OOCR_2)CH_2(OOCR_3)$ (I) wherein $R_1$, $R_2$ and $R_3$ are independently chosen from $C_6$-$C_{30}$ alkyl and $C_6$-$C_{30}$ alkenyl; b) at least one triglyceride oil according to formula (II): $CH_2(OOCR_1)CH(OOCR_2)CH_2(OOCR_3)$ (II) wherein $R_1$, $R_2$ and $R_3$ are independently chosen from $C_6$-$C_{30}$ alkyl and $C_6$-$C_{30}$ alkenyl, at least one of $R_1$, $R_2$ and $R_3$ is substituted with a hydroxyl; c) at least one pasty compound chosen from an ester of dimer dilinoleic acid and polyol(s) or an ester thereof, and d) at least one wax, wherein the triglyceride oil according to formula (I) and the triglyceride oil according to formula (II) are present in the solid anhydrous composition in a weight ratio less than or equal to 1:1.

15 Claims, No Drawings

SOLID ANHYDROUS COMPOSITION FOR CARING FOR AND/OR MAKING UP KERATIN MATERIALS

TECHNICAL FIELD

The present invention relates to a composition for caring for and/or making up keratin materials such as the skin and the lips, preferably the lips. More particularly, the present invention relates to a solid anhydrous composition with desired hardness and leaving a non-sticky feeling upon application onto keratin materials. The present invention also relates to a process for caring for and/or making up keratin materials such as the skin and the lips, preferably the lips.

BACKGROUND

Compositions for caring for and/or making up the skin and/or the lips are produced to satisfy the need of moisturizing or hydration of the skin and the lips.

These compositions in the form of a stick, must, on the one hand, satisfy mechanical requirements in order to ensure the glideness and wear properties of the stick during application and to prevent it from breaking, and, on the other hand, satisfy transfer qualities so as to ensure comfortable application and also a sufficient and good-quality deposit on the lips.

Natural ingredients, i.e., ingredients of natural origin, are of great interest to the consumers. Many oils or pasty compounds with natural origin are used in formulating compositions for caring for and/or making up of skin or lips.

Efforts had been made to formulate compositions comprising natural ingredients, which present good properties as mentioned above.

However, it is difficult to control the hardness of this type of products. A lipstick made of natural ingredients (mainly triglycerids and esters) are often either too hard, which is difficult to apply, or too soft, which is easy to lapse in a container.

In addition, some lipsticks will sweat at higher temperature and leave a sticky film on the lips upon application.

The search consequently continues for compositions with desired hardness and anti-sweating and leaving a non-sticky feeling upon application onto keratin materials.

SUMMARY OF THE INVENTION

The objective of the present invention is thus to overcome the problems described above and to propose a composition with desired hardness and anti-sweating and leaving a non-sticky feeling upon application onto keratin materials.

The above objective is achieved by the present invention, one subject of which is a solid anhydrous composition comprising
a) at least one triglyceride oil according to formula (I):

$$CH_2(OOCR_1)CH(OOCR_2)CH_2(OOCR_3) \quad (I)$$

Wherein $R_1$, $R_2$ and $R_3$ are independently chosen from $C_6$-$C_{30}$ alkyl and $C_6$-$C_{30}$ alkenyl,
b) at least one triglyceride oil according to formula (II):

$$CH_2(OOCR_1)CH(OOCR_2)CH_2(OOCR_3) \quad (II)$$

Wherein $R_1$, $R_2$ and $R_3$ are independently chosen from $C_6$-$C_{30}$ alkyl and $C_6$-$C_{30}$ alkenyl, at least one of $R_1$, $R_2$ and $R_3$ is substituted with a hydroxyl,
c) at least one pasty compound chosen from an ester of dimer dilinoleic acid and polyol(s) or an ester thereof, and
d) at least one wax,
wherein the triglyceride oil according to formula (I) and the triglyceride oil according to formula (II) are present in the solid anhydrous composition in a weight ratio less than or equal to 1:1.

Another subject of the present invention is a process for caring for and/or making up keratin materials such as the skin and the lips, preferably the lips, by applying the solid anhydrous composition as described above to the keratin materials.

It has been found that with the combination of a) at least one triglyceride oil according to formula (I), b) at least one triglyceride oil according to formula (II), c) at least one pasty compound chosen from an ester of dimer dilinoleic acid and polyol(s) or an ester thereof, and d) at least one wax, wherein the triglyceride oil according to formula (I) and the triglyceride oil according to formula (II) are present in the solid anhydrous composition in a weight ratio less than or equal to 1:1, the solid anhydrous composition will have desired hardness and show an improvement against sweating and result in non-sticky feeling upon application onto keratin materials.

In addition, the solid anhydrous composition according to the present invention is easy to apply, i.e. it has good spreadability and pay-off, and would not lapse in a container, i.e., it has good shape stability.

Furthermore, the solid anhydrous composition according to the present invention has homogeneous wear after application.

DETAILD DESCRIPTION OF THE INVENTION

The solid anhydrous composition according to the present invention comprises
a) at least one triglyceride oil according to formula (I):

$$CH_2(OOCR_1)CH(OOCR_2)CH_2(OOCR_3) \quad (I)$$

Wherein $R_1$, $R_2$ and $R_3$ are independently chosen from $C_6$-$C_{30}$ alkyl and $C_6$-$C_{30}$ alkenyl,
b) at least one triglyceride oil according to formula (II):

$$CH_2(OOCR_1)CH(OOCR_2)CH_2(OOCR_3) \quad (II)$$

Wherein $R_1$, $R_2$ and $R_3$ are independently chosen from $C_6$-$C_{30}$ alkyl and $C_6$-$C_{30}$ alkenyl, at least one of $R_1$, $R_2$ and $R_3$ is substituted with a hydroxyl,
c) at least one pasty compound chosen from an ester of dimer dilinoleic acid and polyol(s) or an ester thereof, and
d) at least one wax,
wherein the triglyceride oil according to formula (I) and the triglyceride oil according to formula (II) are present in the solid anhydrous composition in a weight ratio less than or equal to 1:1.

According to a preferred embodiment, all of a) at least one triglyceride oil according to formula (I), b) at least one triglyceride oil according to formula (II), c) at least one pasty compound chosen from an ester of dimer dilinoleic acid and polyol(s) or an ester thereof and d) at least one wax are of plant origin.

The term "solid" used herein means the hardness of the composition at 20° C. and at atmospheric pressure (760 mmHg) is greater than or equal to 30 $Nm^{-1}$ when it is measured according to the protocol described below.

The composition whose hardness is to be determined is stored at 20° C. for 24 hours before measuring the hardness.

The hardness may be measured at 20° C. via the "cheese wire" method, which consists in transversely cutting a wand of product, which is preferably a circular cylinder, by means of a rigid tungsten wire 250 μm in diameter, by moving the wire relative to the stick at a speed of 100 mm/minute.

The hardness of the samples of compositions of the present invention, expressed in $Nm^{-1}$, is measured using a DFGS2 tensile testing machine from the company Indelco-Chatillon.

The measurement is repeated three times and then averaged. The average of the three values read using the tensile testing machine mentioned above, noted Y, is given in grams. This average is converted into Newtons and then divided by L which represents the longest distance through which the wire passes. In the case of a cylindrical wand, L is equal to the diameter (in metres).

The hardness is converted into $Nm^{-1}$ by the equation below:

$$(Y \times 10^{-3} \times 9.8)/L$$

For a measurement at a different temperature, the composition is stored for 24 hours at this new temperature before the measurement.

According to this measuring method, the composition according to the present invention preferably has hardness at 20° C. and at atmospheric pressure of greater than or equal to 40 $Nm^{-1}$ and preferably greater than 50 $Nm^{-1}$.

Preferably, the composition according to the present invention especially has a hardness at 20° C. of less than 500 $Nm^{-1}$, especially less than 400 $Nm^{-1}$ and preferably less than 300 $Nm^{-1}$.

Advantageously, these compositions have a shear value ranging from 75 to 150 and preferably from 100 to 125 gF. Thus, these compositions may be formulated in standard packaging that does not require any composition support means.

For the purposes of the present invention, the term "anhydrous" means that the composition according to the present invention contains less than 2% and preferably less than 0.5% by weight of water relative to the total weight of the composition. Where appropriate, such small amounts of water may be provided by ingredients of the composition that contain it in residual amount, but are not deliberately provided.

Preferably, the "keratin material" according to the present invention is the skin and the lips. By "skin", we intend to mean all the body skin, including the scalp. Still preferably, the keratin material is the lips.

Oil(s)

By "oil" it differs from the pasty compounds or waxes that are described in the present invention, in that the oils are liquid at room temperature (25° C.) and atmospheric pressure (1.013.105 Pa or 760 mmHg).

The composition of the present invention comprises a) at least one triglyceride oil according to formula (I):

$$CH_2(OOCR_1)CH(OOCR_2)CH_2(OOCR_3) \quad (I)$$

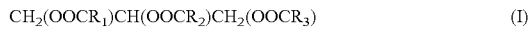

Wherein $R_1$, $R_2$ and $R_3$ are independently chosen from $C_6$-$C_{30}$ alkyl and $C_6$-$C_{30}$ alkenyl.

Preferably, in formula (I), $R_1$, $R_2$ and $R_3$ are independently chosen from $C_6$-$C_{24}$ alkyl and $C_6$-$C_{24}$ alkenyl, preferably $C_6$-$C_{20}$ alkyl and $C_6$-$C_{20}$ alkenyl, more preferably $C_6$-$C_{14}$ alkyl and $C_6$-$C_{14}$ alkenyl, more preferably $C_6$-$C_{12}$ alkyl and $C_6$-$C_{12}$ alkenyl, most preferably $C_6$-$C_{10}$ alkyl and $C_6$-$C_{10}$ alkenyl, said alkyl or alkenyl is linear or branched.

In formula (I), $R_1$, $R_2$ and $R_3$ may be different, or two or all of $R_1$, $R_2$ and $R_3$ may be the same.

Examples of triglyceride oil according to formula (I) are given in the CTFA Cosmetic Ingredient Handbook.

Preferred triglyceride oils according to formula (I) are obtained from carboxylic acids of carbon chain length ranging from $C_6$ to $C_{24}$, preferably from $C_6$ to $C_{20}$, and more preferably from $C_6$ to $C_{18}$, linear or branched, saturated or unsaturated, and glycerol.

More preferably, the triglyceride oils according to formula (I) of the present invention are chosen from triglycerides of fatty acids containing from 6 to 14 carbon atoms, more preferably from 6 to 12 carbon atoms, in particular from 6 to 10 carbon atoms such as triglycerides of heptanoic acid, 2-ethylhexanoic acid, octanoic acids, caprylic acid, capric acid, or mixtures thereof.

In one embodiment, the triglyceride oils according to formula (I) are synthetic.

In another embodiment, the triglyceride oils according to formula (I) are of plant origin. For example, the plant oils that comprise triglyceride oils according to formula (I), or triglyceride oils according to formula (I) obtained from the plant oils can be used.

Vegetable derived triglyceride oils according to formula (I) are particularly preferred, and specific examples of preferred materials as sources of triglyceride oil according to formula (I) include peanut oil, sesame oil, avocado oil, coconut oil, cocoa butter oil, almond oil, safflower oil, corn oil, cotton seed oil, olive oil, jojoba oil, palm oil, soybean oil, wheat germ oil, linseed oil, and sunflower seed oil.

Mentions maybe made of the canola oil, such as that sold under the tradename Lipex Preact by the company AAR-HUSKARL SHAMN.

Preferably, mentions can be made of Caprylic/capric acid triglycerides, such as those sold by the company Stearineries Dubois or those sold under the names Miglyol® 810, 812 and 818, jojoba oil, and shea butter oil. Mentions may also be made of the product sold by the company Wilmar under the name Wilfare Ster MCT, with INCI name caprylic/capric triglyceride.

Advantageously, the at least one triglyceride oil according to formula (I) is present in the composition of the present invention in an amount ranging from 15% to 40% by weight, more preferably from 20% to 35% by weight, relative to the total weight of the composition.

Even more preferably this amount is ranging from 25% to 30% by weight, relative to the total weight of the composition.

The composition of the present invention comprises b) at least one triglyceride oil according to formula (II):

$$CH_2(OOCR_1)CH(OOCR_2)CH_2(OOCR_3) \quad (II)$$

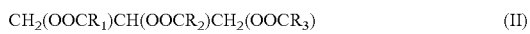

Wherein $R_1$, $R_2$ and $R_3$ are independently chosen from $C_6$-$C_{30}$ alkyl and $C_6$-$C_{30}$ alkenyl, at least one of $R_1$, $R_2$ and $R_3$ is substituted with a hydroxyl.

Preferably, in formula (II), $R_1$, $R_2$ and $R_3$ are independently chosen from $C_6$-$C_{24}$ alkyl and $C_6$-$C_{24}$ alkenyl, preferably $C_6$-$C_{20}$ alkyl and $C_6$-$C_{20}$ alkenyl, more preferably $C_6$-$C_{14}$ alkyl and $C_6$-$C_{14}$ alkenyl, more preferably $C_6$-$C_{12}$ alkyl and $C_6$-$C_{12}$ alkenyl, most preferably $C_6$-$C_{10}$ alkyl and $C_6$-$C_{10}$ alkenyl, wherein at least one of $R_1$, $R_2$ and $R_3$ is substituted with a hydroxyl, said alkyl or alkenyl is linear or branched.

In formula (II), $R_1$, $R_2$ and $R_3$ may be different, or two or all of $R_1$, $R_2$ and $R_3$ may be the same, wherein at least one of $R_1$, $R_2$ and $R_3$ is substituted with a hydroxyl.

Examples of triglyceride oil according to formula (II) are given in the CTFA Cosmetic Ingredient Handbook.

Preferred triglyceride oils according to formula (II) are obtained from carboxylic acids of carbon chain length ranging from $C_6$ to $C_{24}$, preferably from $C_6$ to $C_{20}$, and more preferably from $C_6$ to $C_{18}$, linear or branched, saturated or unsaturated, and glycerol, wherein in addition to carboxylic group, the carboxylic acid contains at least one hydroxyl besides.

More preferably, the triglyceride oils according to formula (II) of the present invention are chosen from triglycerides of fatty acid having a caryboxylic group and at least one hydroxyl containing from 6 to 14 carbon atoms, more preferably from 6 to 12 carbon atoms, in particular from 6 to 10 carbon atoms.

In one embodiment, the triglyceride oils according to formula (II) are synthetic.

In another embodiment, the triglyceride oils according to formula (II) are of plant origin. For example, the plant oils that comprise triglyceride oils according to formula (II), or triglyceride oils according to formula (II) obtained from the plant oils can be used.

Vegetable derived triglyceride oils according to formula (II) are particularly preferred.

Mentions maybe made of *Ricinus communis* (castor) seed oil sold under the tradename Lipovol CO by the company Vantage Specialty Chemicals.

Advantageously, the at least one triglyceride oil according to formula (II) is present in the composition of the present invention in an amount ranging from 20% to 50% by weight, more preferably from 30% to 45% by weight, relative to the total weight of the composition.

Even more preferably this amount is ranging from 35% to 40% by weight, relative to the total weight of the composition.

In the composition of present invention, the triglyceride oil according to formula (I) and the triglyceride oil according to formula (II) are different.

Preferably, the triglyceride oil according to formula (I) and the triglyceride oil according to formula (II) are present in the solid anhydrous composition in a weight ratio of 1:10-1:1, preferably, 1:5-1:1, more preferably 1:3-6:7, most preferably 1:2-4:5.

According to a preferred embodiment, the composition of the present invention may further comprise additional oils.

Oils may comprise nonvolatile oils and volatile oils. The term "nonvolatile oil" means an oil that remains on the skin or the keratin fibre at room temperature and atmospheric pressure. More specifically, a nonvolatile oil has an evaporation rate strictly less than 0.01 mg/cm$^2$/min.

To measure this evaporation rate, 15 g of oil or of oil mixture to be tested are placed in a crystallizing dish 7 cm in diameter, which is placed on a balance in a large chamber of about 0.3 m$^3$ that is temperature-regulated, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing said oil or said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit of area (cm$^2$) and per unit of time (minutes).

The term "volatile oil" means any non-aqueous medium that is capable of evaporating on contact with the skin or the lips in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits included.

The oils may be silicone oil, fluoro oil, hydrocarbon-based oil, or a mixture thereof.

For the purposes of the present invention, the term "silicone oil" means an oil comprising at least one silicon atom, and especially at least one Si—O group.

The term "fluoro oil" means an oil comprising at least one fluorine atom.

The term "hydrocarbon-based oil" here means an oil mainly containing hydrogen and carbon atoms other than the triglyceride oil according to formula (I) and the triglyceride oil according to formula (II) as defined above.

The oils may optionally comprise oxygen, nitrogen, sulfur and/or phosphorus atoms, for example in the form of hydroxyl or acid radicals.

The oil may be chosen from polar oils, apolar oils, or mixtures thereof.

For the purposes of the present invention, the term "polar oil" means an oil whose solubility parameter at 25° C., δa, is other than 0 (J/cm$^3$)$^{1/2}$.

For the purposes of the present invention, the term "apolar oil" means an oil whose solubility parameter at 25° C., δa, is equal to 0 (J/cm$^3$)$^{1/2}$.

The definition and calculation of the solubility parameters in the Hansen three-dimensional solubility space are described in the article by C.M. Hansen: "The three dimensional solubility parameters", J. Paint Technol. 39, 105 (1967).

According to this Hansen space:

δD characterizes the London dispersion forces derived from the formation of dipoles induced during molecular impacts;

δp characterizes the Debye interaction forces between permanent dipoles and also the Keesom interaction forces between induced dipoles and permanent dipoles;

δh characterizes the specific interaction forces (such as hydrogen bonding, acid/base, donor/acceptor, etc.); and δa is determined by the equation: $δa=(δp^2 δh^2)^{1/2}$.

The parameters δp, δh, δD and δa are expressed in (J/cm$^3$)$^{1/2}$.

According to a more preferred embodiment, the additional oils, when existing, are chosen from nonvolatile hydrocarbon-based oil, more preferably of plant origin.

In particular, the nonvolatile hydrocarbon-based oil of plant origin may be chosen from the list of oils below, and mixtures thereof:

plant oils which are different from the ones described before, such as *Linum usitatissimum* (linseed) oil, *Macadamia ternifolia* seed oil, *Limnanthes alba* (meadowfoam) seed oil, *Oryza sativa* (rice) bran oil, *Bertholletia excels* seed oil.

nonvolatile oils of high molecular mass, which are of plant origin or obtained from plants, for example between 350 and 10 000 g/mol, for instance:

a) linear fatty acid esters with a total carbon number ranging from 35 to 70, for instance pentaerythrityl tetrapelargonate (MW=697.05 g/mol), b) hydroxylated esters such as polyglycerol-2 triisostearate (MW=965.58 g/mol);

c) esters of $C_{24}$-$C_{28}$ branched fatty acids or fatty alcohols such as those described in patent application EP-A-0 955 039, and especially triisoarachidyl citrate (MW=1033.76 g/mol), pentaerythrityl tetraisononanoate (MW=697.05 g/mol), glyceryl triisostearate (MW=891.51 g/mol), pentaerythrityl tetraisostearate (MW=1202.02 g/mol), polyglyceryl-2 tetraisostearate (MW=1232.04 g/mol) or else pentaerythrityl tetrakis(2-decyl)tetradecanoate (MW=1538.66 g/mol), and mixtures thereof.

According to a preferred embodiment, the amount of the oils, including the triglyceride oil according to formula (I) and the triglyceride oil according to formula (II) as described above, in the composition of the present invention may range from 50% to 85% by weight, preferably from 60% to 80% by weight, more preferably from 70% to 80% relative to the total weight of the composition.

Pasty Compound(s)

The term "pasty compound" used herein is understood to mean a lipophilic fatty compound with a reversible solid/liquid change of state exhibiting, in the solid state, an anisotropic crystalline arrangement and comprising, at a temperature of 23° C., a liquid fraction and a solid fraction.

In other words, the starting melting temperature of the pasty compound is less than 23° C. The liquid fraction of the pasty compound, measured at 23° C., represents 9 to 97% by weight of the composition. This liquid fraction at 23° C. preferably represents between 15 and 85%, more preferably between 40 and 85%, by weight.

The melting point of a solid fatty substance can be measured using a differential scanning calorimeter (DSC), for example the calorimeter sold under the name "DSC Q100" by the company TA Instruments with the software "TA Universal Analysis".

The measurement protocol is as follows:

A solid fat sample of about 5 mg is placed in a crucible "hermetic aluminum capsule" When the solid fatty substance is soft (pasty fatty compound), the sample is subjected to a first rise in temperature ranging from 20° C. to 80° C., at the heating rate from 2° C./minute to 80° C., then left to the isotherm of 80° C. for 20 minutes, then cooled from 80° C. to −80° C. at a cooling rate of 2° C./minute, and finally subjected to a second temperature rise from −80° C. to 20° C. at a heating rate of 2° C./minute.

The melting temperature value of the solid fatty substance is the value of the peak of the most endothermic peak of the observed melting curve, representing the variation of the difference in power absorbed as a function of temperature."

According to the present invention, the composition comprises at least one pasty compound chosen from an ester of dimer dilinoleic acid and polyol(s) or an ester thereof.

In the expression "an ester of dimer dilinoleic acid and polyol(s) or an ester thereof", the term "an ester thereof" is intended to denote one of the derivatives of these dimer dilinoleic acid esters of polyol(s) obtained either by reaction of alcohol function(s) of the polyol, which are not employed in bonds of ester type with acid functions of the dilinoleic acid, with one or more carboxylic functions of acid molecules other than dilinoleic acid or alternatively by reaction of acid functions of the dilinoleic dimer, which are not employed in bonds of ester type with alcohol functions of the polyol, with alcohol functions of alcohol molecules other than the polyol.

Dimer Dilinoleic Acid

The dimer dilinoleic acid that is suitable for use in the present invention may be obtained by polymerization reaction, especially by intermolecular dimerization of at least one linoleic acid.

The oxidation stability of the compound may be improved by hydrogenating the double bonds remaining after the dimerization reaction.

The linoleic acid dimer may also be obtained by dimerization of the hydrogenated form of linoleic acid.

The hydrogenated form of the acid or of the diacid may be partial or total, and may correspond, for example, to the saturated form, which is more oxidation-stable.

As indicated previously, the carboxylic functions of the dimer dilinoleic acid residue not engaged in the ester bond with the polyol residue (s) may be engaged in other ester bonds with other alcohol functions of alcohol molecules other than the polyol(s).

These alcohol molecules or residues may be monoalcohols or polyols.

As examples of alcohol residues that are suitable for use in the invention, mention may be made of hydrocarbon-based compounds comprising a hydroxyl function and containing from 4 to 40 carbon atoms, in particular from 6 to 36 carbon atoms, in particular from 8 to 32 carbon atoms, in particular from 16 to 28 carbon atoms and more particularly from 18 to 24 carbon atoms.

As examples of monoalcohols that are suitable for the invention, mention may be made, in a non-limiting manner, of butanol, pentanol, propanol, hexanol, heptanol, octanol, decanol, dodecanol, hexadecanol, octadecanol, eicosadecanol, phytosterol, isostearol, stearol, cetol, behenol, etc.

Polyol(s)

The term "polyol" is intended to denote any hydrocarbon-based compound comprising at least two hydroxyl functions and containing from 4 to 40 carbon atoms, in particular from 6 to 36 carbon atoms, in particular from 8 to 32 carbon atoms, in particular from 16 to 28 carbon atoms and more particularly from 18 to 24 carbon atoms. The hydrocarbon-based chains may be interrupted, where appropriate, by the presence of at least one hetero atom, and especially an oxygen atom.

A polyol or a polyol ester that is suitable for use in the present invention may comprise, for example, from 2 to 12 hydroxyl functions, in particular from 2 to 8 hydroxyl functions, and more particularly from 4 to 6 hydroxyl functions.

Where appropriate, the hydroxyl functions, other than those already employed in an ester bond with the dimer dilinoleic acid, may also be employed, wholly or partly with other ester bonds via reactivity with acid molecules other than the dimer dilinoleic acid. The polyol or an ester thereof that is suitable for use in the present invention may be chosen especially from linear, branched, cyclic or polycyclic, saturated or unsaturated alcohols.

Thus, the polyol may be chosen, for example, from a diol, a triol, a tetraol, or a pentaol, or an ester thereof.

The polyol may be a diol, or an ester thereof, chosen especially from a fatty alcohol dimer, a monoglycerol or polyglycerol, a $C_{2-4}$ monoalkylene or polyalkylene glycol, 1,4-butanediol and pentaerythritol.

As examples of diols that are also suitable for use in the invention, mention may be made, in a non-exhaustive manner, of butanediol, pentanediol, propanediol, hexanediol, hexylene glycol, heptanediol, octanediol, nonanediol, decanediol, 1-decanediol, dodecanediol, tridecanediol, tetradecanediol, pentadecanediol, hexadecanediol, nonadecanediol, octadecanediol, cyclohexanediol, diglycerol, erythritol, pentaerythritol, xylitol, sorbitol, ethylene glycol and xylene glycol, and isomers thereof.

A fatty alcohol dimer may also be the product of hydrogenation, for example catalytic hydrogenation, of a fatty acid dimer, which is itself obtained by dimerization of at least one unsaturated fatty acid, especially of $C_8$ to $C_{34}$, especially of $C_{12}$ to $C_{22}$, in particular of $C_{16}$ to $C_{20}$ and more particularly of $C_{18}$.

According to one particular embodiment, a fatty alcohol dimer may be a diol dimer that can be the product of hydrogenation of dilinoleic diacid. It may be in a saturated form.

A fatty alcohol dimer may be, for example, a dilinoleol dimer.

As an example of a diol that may be suitable for use in the invention, mention may be made especially of diglycerol.

This compound is a glycerol dimer resulting from the condensation of two molecules of glycerol, with the loss of a water molecule.

The term "diglycerol" denotes any isomer combination that can result from such a condensation, for instance linear isomers, branched isomers and, where appropriate, cyclic isomers resulting from an intramolecular dehydration of a diglycerol molecule.

The diglycerol may be obtained via any process known to those skilled in the art and especially those described in patent EP 0 750 848.

As examples of acid molecules that can interact with one or more hydroxyl functions of the polyol, not employed in the ester bond with the dimer dilinoleic acid, mention may be made, in a non-limiting manner, of molecules derived from isostearic acid, behenic acid, phytosteric acid, stearic acid or cetylic acid.

An ester of dimer dilinoleic acid and polyol(s) that is suitable for use in the present invention may be obtained by reacting a polyol or an ester thereof with a dimer dilinoleic acid, in a molar ratio of about 1.0:0.2-1.0.

An ester that may be suitable for use in the present invention may especially be obtained by reacting a dimer dilinoleic acid with a dilinoleol and, where appropriate, at least one additional monoalcohol chosen especially from behenol, isostearol, phytosterol, stearol and cetol, and mixtures thereof.

Thus, an ester used in the context of the present invention may be used in the form of a mixture of various esters, for example.

An ester of dimer dilinoleic acid and polyol(s) or an ester thereof that is suitable for the invention may be obtained, for example, by reacting a glycerol, an isostearic acid and a dimer dilinoleic acid, especially, in a molar ratio of 1.0:0.2-1.0:0.5-0.9.

As examples of an ester of dimer dilinoleic acid and polyol(s) or an ester thereof suitable for the invention, mention may be made of the esters described in patent applications JP 2004-256515 and JP 2005-179377.

An ester of dimer dilinoleic acid and polyol(s) or an ester thereof suitable for use in the present invention may have a molecular weight ranging from about 2000 to about 25 000 g/mol, in particular from about 4000 to about 20 000 g/mol, in particular from about 7000 to about 15 000 g/mol and more particularly from about 8000 to about 10 000 g/mol.

According to one embodiment, an ester in accordance with the invention may comprise an alternating sequence of dimer dilinoleate residue(s) and of residue (s) related to said polyol(s), and especially to the said diol(s), said polyols or diols being, for example, as defined above.

Thus, in such a configuration, each of the two ends of the said sequence may bear, respectively, a unit OR' and OR" with R' and R" representing, independently of each other, a hydrogen atom or OR' and OR" representing, independently of each other, a $C_2$ to $C_{36}$, especially $C_8$ to $C_{24}$, in particular $C_{12}$ to $C_{20}$ and more particularly $C_{16}$ to $C_{18}$ hydrocarbon-based monoalcohol residue.

According to one embodiment, R' and R" may both represent a hydrogen atom.

According to one embodiment, OR' and OR" may both represent an identical or different hydrocarbon-based mono-alcohol residue.

As examples of hydrocarbon-based monoalcohol residues OR' and OR" that may be suitable for the invention, mention may be made of fatty alcohol residues.

According to one embodiment, an ester of dimer dilinoleic acid and polyol(s) or an ester thereof that may be suitable for use in the present invention may have the general formula (III) below:

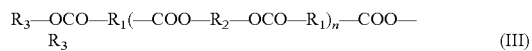

(III)

In which:

$COR_1CO$ represents a dimer dilinoleate residue, $OR_2O$ represents a fatty alcohol dimer residue ranging from $C_{16}$ to $C_{68}$, especially from $C_{24}$ to $C_{44}$, in particular from $C_{32}$ to $C_{40}$ and more particularly may be of $C_{36}$.

$OR_3$ represents a monoalcohol residue ranging from 4 to 40 carbon atoms, in particular from 6 to 36 carbon atoms, in particular from 8 to 32, in particular from 16 to 28, and more particularly from 18 to 24 carbon atoms, and n is an integer ranging from 1 to 15, in particular from 2 to 10 and more particularly from 5 to 7.

According to one embodiment, $OR_2O$ may represent a dimer dilinoleyl residue.

Moreover, $OR_3$ may represent a hydrocarbon-based monoalcohol residue chosen, for example, from behenyl, isostearyl and phytosteryl residues, and mixtures thereof.

According to another embodiment, the ester of dimer dilinoleic acid and polyol(s) or an ester thereof that may be suitable for use in the invention may, especially, have the general formula (IV) below:

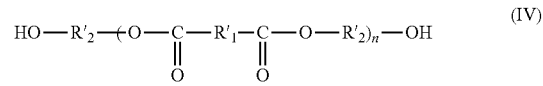

(IV)

In which:

n is an integer ranging from 1 to 15, especially from 2 to 10 and in particular from 5 to 7;

$OCR'_1CO$ represents a dimer dilinoleate residue, $OR'_2O$ represents a diglyceryl residue of general formula (V) below:

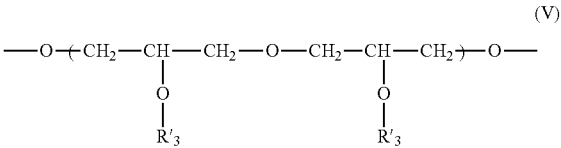

(V)

In which:

$R'_3$ represents H or $OR'_3$ represents a fatty acid residue that may range from $C_8$ to $C_{34}$, especially from $C_{12}$ to $C_{22}$, in particular of $C_{16}$ to $C_{20}$ and more particularly may be $C_{18}$.

According to one embodiment, the fatty acid residue represented by $OR'_3$ may be an isostearyl residue.

The viscosity of an ester of dimer dilinoleic acid and polyol(s) or an ester thereof, according to the invention, may be measured according to any process known to those skilled in the art, and especially according to the conventional process described hereinbelow.

The viscosity may be measured using a cone/plate or parallel plate viscometer of Ares type (TA-Instrument) operating in kinetic sweep mode over a shear range of about 1-1000 s$^{-1}$ to induce a flow tension at about 1000 Pa.

The cone/plate or parallel plates may consist of a material selected from the group constituted of stainless steel, acrylic resins or polyphenylene sulfide (PPS resin).

The cone/plate diameter may be 25 mm (cone angle 0.10 radiants).

The measurement is performed at about 25° C.

Before any measurement, the stability of the sample is checked by means of the dynamic sweep period test, which makes it possible to determine if the sample is stable per se.

The shear viscosity is determined using the ETA value in the plateau region according to the flow.

The dynamic sweep period is determined at a frequency of 1.0 Hz over a period of 600 seconds.

The measurements at constant sweep rate are performed with a rate ranging from 1.0 to 1000 s$^{-1}$ and in particular from 1.0 to 100 s$^{-1}$.

The viscosity of an ester of dimer dilinoleic acid and polyol(s) or an ester thereof suitable for use in the invention may range from about 20 000 mPa·s to about 150 000 mPa·s, especially from about 40 000 mPa·s to about 100 000 mPa·s and in particular from about 60 000 mPa·s to about 80 000 mPa·s.

An ester of dimer dilinoleic acid and polyol(s) or an ester thereof that is suitable for the invention may be chosen especially from the esters having the following INCI nomenclature: polyglyceryl-2 isostearate dimer dilinoleate copolymer, bis-behenyl/isostearyl/phytosteryl dimer dilinoleyl dimer dilinoleate, and mixtures thereof.

Such compounds may be obtained, for example, under the reference Hailucent ISDA (Kokyu Alcohol) and Plandool-G (Nippon Fine Chemical Company Ltd).

An ester of dimer dilinoleic acid and polyol(s) or an ester thereof suitable for use in the invention may be advantageously present in the composition according to the invention in an amount sufficient to give these compositions improved cosmetic properties, especially in terms of mean gloss staying power.

Advantageously, the at least one pasty compound chosen from an ester of dimer dilinoleic acid and polyol(s) or an ester thereof is present in the composition of the present invention in an amount ranging from 5% to 15% by weight, relative to the total weight of the composition.

According to an embodiment, the at least one pasty compound chosen from an ester of dimer dilinoleic acid and polyol(s) or an ester thereof is present in the composition of the present invention in an amount ranging from 6% to 12% by weight, more preferably from 7% to 10% by weight, relative to the total weight of the composition.

Alternatively, the composition according to the present invention can further comprises additional pasty compound chosen from polyol ethers, which is, in particular, polyalkylene glycol pentaerythritol ethers.

The polyalkylene glycol pentaerythritol ethers may contain in particular from 1 to 450 oxyalkylenated units, preferably from 1 to 200 oxyalkylenated units, even better from 1 to 100 oxyalkylenated units and better still from 1 to 50 oxyalkylenated units. They may be chosen in particular from polyethylene glycol pentaerythritol ethers containing from 1 to 450 oxyethylenated units, preferably from 1 to 200 oxyethylenated units, even better from 1 to 100 oxyethylenated units and better still from 1 to 50 oxyethylenated units; polypropylene glycol pentaerythritol ethers containing from 1 to 450 oxypropylenated units, preferably from 1 to 200 oxypropylenated units, even better from 1 to 100 oxypropylenated units and better still from 1 to 50 oxypropylenated units; and mixtures thereof. According to a preferred embodiment of the invention, use is made of the polyethylene glycol pentaerythrityl ether containing 5 oxyethylenated units (5 EO) (CTFA name: PEG-5 Pentaerythrityl Ether), the polypropylene glycol pentaerythritol ether containing 5 oxypropylenated units (5 PO) (CTFA name: PPG-5 Pentaerythrityl Ether), and mixtures thereof, and more especially the PEG-5 Pentaerythrityl Ether, PPG-5 Pentaerythrityl Ether and soya bean oil mixture marketed under the name "Lanolide" by the company Vevy, a mixture in which their constituents are in a 46/46/8 weight ratio: 46% of PEG-5 Pentaerythrityl Ether, 46% of PPG-5 Pentaerythrityl Ether and 85% of soya bean oil.

More preferably the composition of the present invention comprises at least one pasty compound chosen from polyol ethers comprising polyethylene glycol pentaerythrityl ether containing 5 oxyethylenated units, polypropylene glycol pentaerythritol ether containing 5 oxypropylenated units, and mixtures thereof.

Even more preferably, the pasty compound is a polyol ether in the form of a mixture comprising polyethylene glycol pentaerythritol ether comprising 5 oxyethylenated units, polypropylene glycol pentaerythritol ether comprising 5 oxypropylenated units, and soya bean oil.

Such products are commercially available, for example, marketed under the name "Lanolide" by the company Vevy, a mixture in which their constituents are in a 46/46/8 weight ratio: 46% of PEG-5 Pentaerythrityl Ether, 46% of PPG-5 Pentaerythrityl Ether and 8% of soya bean oil.

The composition of the present invention can further comprise at least one chosen from hydrocarbon based pasty compounds and more particularly from the following compounds:

lanolin and derivatives thereof;

petroleum jelly, in particular the product whose INCI name is petrolatum and which is sold under the name Ultima White PET USP by the company Calumet Specialty, vinyl polymers, especially:

olefin homopolymers and copolymers, hydrogenated diene homopolymers and copolymers, linear or branched oligomers, homopolymers and copolymers of alkyl (meth)acrylates preferably containing a $C_8$-$C_{30}$ alkyl group, oligomers, homopolymers and copolymers of vinyl esters containing $C_8$-$C_{30}$ alkyl groups, such as vinyl ester homopolymers containing $C_8$-$C_{30}$ alkyl groups, such as polyvinyl laurate (sold especially under the reference Mexomer PP by the company Chimex) and arachidyl propionate sold under the brand name Waxenol 801 by Alzo;

oligomers, homopolymers and copolymers of vinyl ethers containing $C_8$-$C_{30}$ alkyl groups;

liposoluble polyethers resulting from the polyetherification between one or more $C_2$-$C_{100}$ and preferably $C_2$-$C_{50}$ diols, among the liposoluble polyethers that are particularly preferred are copolymers of ethylene oxide and/or of propylene oxide with $C_6$-$C_{30}$ long-chain alkylene oxides, more preferably such that the weight ratio of the ethylene oxide and/or of the propylene oxide to the alkylene oxides in the copolymer is from 5:95 to 70:30. In this family, mention will be made especially of copolymers such that the long-chain alkylene oxides are arranged in blocks having an average molecular weight from 1000 to 10 000, for example a polyoxyethylene/polydodecyl glycol block copolymer such as the ethers of dodecanediol (22 mol) and of polyethylene glycol (45 OE) sold under the brand name Elfacos ST9 by Akzo Nobel.

esters especially those chosen from:

esters of a glycerol oligomer, especially diglycerol esters, in particular condensates of adipic acid and of glycerol, for which some of the hydroxyl groups of the glycerols have reacted with a mixture of fatty acids such as stearic acid, capric acid, stearic acid and isostearic acid, and 12-hydroxystearic acid, preferably such as bis-diglyceryl polyacyladipate-2 sold under the brand name Softisan® 649 by the company Cremer Oleo, vinyl ester homopolymers containing $C_8$-$C_{30}$ alkyl groups, such as polyvinyl laurate (sold especially under the reference Mexomer PP by the company Chimex) and arachidyl propionate sold under the brand name Waxenol 801 by Alzo, phytosterol esters, fatty acid triglycerides and derivatives thereof, for instance triglycerides of fatty acids, which are especially $C_{16}$-$C_{24}$, and partially or totally hydrogenated such as those sold under the reference Softisan 100 by the company Sasol, pentaerythritol esters, noncrosslinked polyesters resulting from polycondensation between a linear or branched $C_4$-$C_{50}$ dicarboxylic acid or polycarboxylic acid and a $C_2$-$C_{50}$ diol or polyol, aliphatic esters of an ester, resulting from the esterification of an aliphatic hydroxycarboxylic acid ester with an aliphatic carboxylic acid comprising from 4 to 30 carbons, preferably 8 to 30 carbons. It is preferably chosen from hexanoic acid, heptanoic acid, octanoic acid, 2-ethylhexanoic acid, nonanoic acid, decanoic acid, undecanoic acid, dodecanoic acid, tridecanoic acid, tetradecanoic acid, pentadecanoic acid, hexadecanoic acid, hexyldecanoic acid, heptadecanoic acid, octadecanoic acid, isostearic acid, nonadecanoic acid, eicosanoic acid, isoarachidic acid, octyldodecanoic acid, heneicosanoic acid and docosanoic acid, and mixtures thereof. The aliphatic carboxylic acid is preferably branched. The aliphatic hydroxycarboxylic acid ester is advantageously derived from a hydroxylated aliphatic carboxylic acid containing from 2 to 40 carbon atoms, preferably from 10 to 34 carbon atoms and better still from 12 to 28 carbon atoms, and from 1 to 20 hydroxyl groups, preferably from 1 to 10 hydroxyl groups and better still from 1 to 6 hydroxyl groups. The aliphatic hydroxycarboxylic acid ester is chosen from:

partial or total esters of saturated linear mono-hydroxylated aliphatic monocarboxylic acids;

partial or total esters of unsaturated monohydroxylated aliphatic monocarboxylic acids;

partial or total esters of saturated monohydroxylated aliphatic polycarboxylic acids;

partial or total esters of saturated polyhydroxylated aliphatic polycarboxylic acids;

partial or total esters of $C_2$ to $C_{16}$ aliphatic polyols that have reacted with a monohydroxylated or polyhydroxylated aliphatic monocarboxylic or polycarboxylic acid, and mixtures thereof.

mango butter, such as the product sold under the reference Lipex 203 by the company AarhusKarlshamn, shea butter in particular the product whose INCI name is *Butyrospermum parkii* Butter, such as the product sold under the reference Sheasoft® by the company Aarhuskarlshamn, and mixtures thereof.

According to a preferred embodiment, the amount of the pasty compound, including the ester of dimer dilinoleic acid and polyol(s) or an ester thereof as described above, in the composition of the present invention may range from 5% to 20% by weight, more preferably from 6% to 15% by weight, relative to the total weight of the composition.

Wax(es)

The wax under consideration in the context of the present invention is generally a lipophilic compound that is solid at room temperature (25° C.), with a solid/liquid reversible change of state, having a melting point of greater than or equal to 30° C., preferably greater than or equal to 40° C., which may be up to 200° C. and in particular up to 120° C.

The melting point of can be measured using a differential scanning calorimeter (DSC), for example the calorimeter sold under the name "DSC Q100" by the company TA Instruments with the software "TA Universal Analysis" according to the protocol already described.

For the purposes of the invention, the waxes have melting points of between 38° C. and 90° C. Preferably, a wax is said to be in the solid state when all of its mass is in solid crystalline form at room temperature.

The waxes that may be used in a composition according to the present invention are chosen from solid waxes that may or may not be deformable at room temperature of animal, plant, mineral or synthetic origin, and mixtures thereof, preferably chosen from wax of animal or plant origin.

Hydrocarbon-based waxes, for instance beeswax, lanolin wax or Chinese insect wax; rice wax, carnauba wax, candelilla wax, ouricury wax, esparto grass wax, cork fibre wax, sugar cane wax, Japan wax and sumach wax, *Helianthus annuus* (sunflower) seed wax; montan wax, microcrystalline waxes, paraffins and ozokerite; polyethylene waxes, polymethylene waxes, the waxes obtained by Fisher-Tropsch synthesis and waxy copolymers, and also esters thereof, may especially be used.

Mentions may be especially made of beeswax, for example the product sold under the trade name Cire d'abelle blanche BR G889 by Koster Keunen, carnauba wax, for example sold under the name Cerauba T1 Bio by the company Baerlocher. *Helianthus annuus* (sunflower) seed wax sold under the name Sunflower Wax by the company Koster Keunen, or a mixture thereof.

Mention may also be made of waxes obtained by catalytic hydrogenation of animal or plant oils containing linear or branched $C_6$-$C_{32}$ fatty chains.

Among these waxes that may especially be mentioned are hydrogenated jojoba oil, hydrogenated sunflower oil, hydrogenated castor oil, hydrogenated coconut oil, hydrogenated lanolin oil, bis(1,1,1-trimethylolpropane) tetrastearate sold under the name Hest 2T-4S by the company Heterene, and bis(1,1,1-trimethylolpropane) tetrabehenate sold under the name Hest 2T-4B by the company Heterene.

As for esters obtained by catalytic hydrogenation of animal or plant oils, mention may be made to the waxes obtained by hydrogenation of palm oil esterified with cetyl alcohol. Such products can be found, for example, under the trade name CUTINA® CP from Cognis (BASF), castor oil esterified with cetyl alcohol, sold under the names Phytowax ricin 16L64® and 22L73® by the company Sophim, may also be used. Such waxes are described in patent application FR-A-2 792 190.

A wax that may be used is a $C_{20}$-$C_{40}$ alkyl (hydroxystearyloxy)stearate (the alkyl group containing from 20 to 40 carbon atoms), alone or as a mixture. Such a wax is especially sold under the names Kester Wax K 82 P®, Hydroxypolyester K 82 P® and Kester Wax K 80 P® by the company Koster Keunen.

Advantageously, the wax(es) suitable for the present invention is chosen from hydrocarbon-based waxes, esters obtained by catalytic hydrogenation of animal or plant oils, or a mixture thereof.

More preferably, the composition of the present invention comprises at least one wax chosen from carnauba wax, *Helianthus annuus* (sunflower) seed wax, or a mixture thereof.

According to one preferred embodiment, the composition according to the invention comprises the wax(es) in an amount ranging from 5% to 15% by weight, preferably from 6% to 12% by weight, most preferably from 7% to 10% by weight, relative to the total weight of the composition. According to a preferred embodiment, the weight ratio of the triglyceride oil according to formula (I) and the triglyceride oil according to formula (II): the at least one pasty compound(s) chosen from an ester of dimer dilinoleic acid and polyol(s) or an ester thereof ranges from 3:1 to 10:1, preferably from 5:1 to 9:1, more preferably from 6:1 to 8:1.

Dyestuff

The solid anhydrous composition in accordance with the present invention may optionally comprise at least one dyestuff, which may be chosen from water-soluble or water-insoluble, liposoluble or non-liposoluble, organic or mineral dyestuffs, and materials with an optical effect, and mixtures thereof. Preferably, the amount of dyestuff is below 20% by weight relative to the total weight of the composition.

For the purposes of the present invention, the term "dyestuff" means a compound that is capable of producing a coloured optical effect when it is formulated in sufficient amount in a suitable cosmetic medium.

Preferably, the composition according to the present invention comprises at least one dyestuff, chosen from pigments and/or nacres and/or water-soluble dyes, and mixtures thereof.

According to one preferred embodiment, a composition according to the present invention comprises at least one water-soluble dyestuff.

The water-soluble dyestuffs used according to the present invention are more particularly water-soluble dyes.

For the purposes of the present invention, the term "water-soluble dye" is intended to mean any natural or synthetic, generally organic compound, which is soluble in an aqueous phase or water-miscible solvents and which is capable of colouring. In particular, the term "water-soluble" is intended to mean the capacity of a compound to be dissolved in water, measured at 25° C., to a concentration at least equal to 0.1 g/l (production of a macroscopically isotropic, transparent, coloured or colourless solution). This solubility is in particular greater than or equal to 1 g/l.

As water-soluble dyes that are suitable for use in the present invention, mention may be made in particular of synthetic or natural water-soluble dyes, for instance FDC Red 4 (CI: 14700), DC Red 6 (Lithol Rubine Na; CI: 15850), DC Red 22 (CI: 45380), DC Red 28 (CI: 45410 Na salt), DC Red 30 (CI: 73360), DC Red 33 (CI: 17200), DC Orange 4 (CI: 15510), FDC Yellow 5 (CI: 19140), FDC Yellow 6 (CI: 15985), DC Yellow 8 (CI: 45350 Na salt), FDC Green 3 (CI: 42053), DC Green 5 (CI: 61570), FDC Blue 1 (CI: 42090).

As non-limiting illustrations of sources of water-soluble dyestuff(s) that may be used in the context of the present invention, mention may be made especially of those of natural origin, such as extracts of cochineal carmine, of beetroot, of grape, of carrot, of tomato, of annatto, of paprika, of henna, of caramel and of curcumin.

Thus, the water-soluble dyestuffs that are suitable for use in the present invention are especially carminic acid, betanin, anthocyans, enocyanins, lycopene, (3-carotene, bixin, norbixin, capsanthin, capsorubin, flavoxanthin, lutein, cryptoxanthin, rubixanthin, violaxanthin, riboflavin, rhodoxanthin, cantaxanthin and chlorophyll, and mixtures thereof.

They may also be copper sulfate, iron sulfate, water-soluble sulfopolyesters, rhodamine, betaine, methylene blue, the disodium salt of tartrazine and the disodium salt of fuchsin.

Some of these water-soluble dyestuffs are in particular permitted for food use. Representatives of these dyes that may be mentioned more particularly include dyes of the carotenoid family, referenced under the food codes E120, E162, E163, E160a-g, E150a, E101, E100, E140 and E141.

According to one preferred variant, the water-soluble dyestuff(s) that are to be transferred onto the skin and/or the lips intended to be made up are formulated in a physiologically acceptable medium so as to be compatible with impregnation into the substrate.

The water-soluble dyestuff(s) may be present in the composition according to the present invention in a content ranging from 1% to 15% by weight and preferably from 2% to 10% by weight relative to the total weight of the composition.

According to another embodiment, the composition according to the present invention may comprise at least one pigment and/or nacre as dyestuff.

The term "pigments" should be understood as meaning white or coloured, inorganic (mineral) or organic particles, which are insoluble in the liquid organic phase, and which are intended to colour and/or opacify the composition and/or the deposit produced with the composition.

The pigments may be chosen from mineral pigments, organic pigments and composite pigments (i.e. pigments based on mineral and/or organic materials).

The pigments may be chosen from monochromatic pigments, lakes, nacres, and pigments with an optical effect, for instance reflective pigments and goniochromatic pigments.

The mineral pigments may be chosen from metal oxide pigments, chromium oxides, iron oxides, titanium dioxide, zinc oxides, cerium oxides, zirconium oxides, manganese violet, Prussian blue, ultramarine blue and ferric blue, and mixtures thereof.

The organic pigments may be, for example:
cochineal carmine,
organic pigments of azo dyes, anthraquinone dyes, indigoid dyes, xanthene dyes, pyrene dyes, quinoline dyes, triphenylmethane dyes or fluoran dyes,
organic lakes or insoluble sodium, potassium, calcium, barium, aluminum, zirconium, strontium or titanium salts of acidic dyes such as azo, anthraquinone, indigoid, xanthene, pyrene, quinoline, triphenylmethane or fluoran dyes. These dyes generally comprise at least one carboxylic or sulfonic acid group;
melanin-based pigments.

Among the organic pigments, mention may be made of D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5 and FD&C Yellow No. 6.

For the purposes of the present patent application, the term "nacre" is intended to mean coloured particles of any form, which may or may not be iridescent, in particular produced by certain mollusks in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, titanium mica coated with an organic dye in particular of the abovementioned type, and also nacreous pigments based on bismuth oxychloride. They may also be mica particles, at the surface of which are superposed at least two successive layers of metal oxides and/or of organic dyestuffs.

The nacres may more particularly have a yellow, pink, red, bronze, orangey, brown, gold and/or coppery colour or tint.

As illustrations of nacres that may be introduced as interference pigments into the composition, mention may be made of the gold-coloured nacres sold in particular by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold in particular by the company Merck under the name Bronze fine (17384) (Colorona) and Bronze (17353) (Colorona) and by the company Engelhard under the name Super bronze (Cloisonne); the orange nacres sold in particular by the company Engelhard under the name Orange 363C (Cloisonne) and Orange MCR 101 (Cosmica) and by the company Merck under the name Passion orange (Colorona) and Matte orange (17449) (Microna); the brown nacres sold in particular by the company Engelhard under the name Nu-antique copper 340XB (Cloisonne) and Brown CL4509 (Chromalite); the nacres with a copper tint sold in particular by the company Engelhard under the name Copper 340A (Timica); the nacres with a red tint sold in particular by the company Merck under the name Sienna fine (17386) (Colorona); the nacres with a yellow tint sold in particular by the company Engelhard under the name Yellow (4502) (Chromalite); the red nacres with a gold tint sold in particular by the company Engelhard under the name Sunstone G012 (Gemtone); the pink nacres sold in particular by the company Engelhard under the name Tan opale G005 (Gemtone); the black nacres with a gold tint sold in particular by the company Engelhard under the name Nu antique bronze 240 AB (Timica), the blue nacres sold in particular by the company Merck under the name Matte blue (17433) (Microna), the white nacres with a silvery tint sold in particular by the company Merck under the name Xirona Silver, and the golden-green pink-orange nacres sold in particular by the company Merck under the name Indian summer (Xirona), and mixtures thereof.

Additives

In a particular embodiment, a solid anhydrous composition according to the present invention may further comprise at least one additive usually used in the field under consideration. In particular the additive is chosen from gums, anionic, cationic, amphoteric or nonionic surfactants, silicone surfactants, resins, thickening agents, dispersants, antioxidants, preserving agents, fragrances, neutralizers, antiseptics, additional cosmetic active agents, such as vitamins, moisturizers, emollients or collagen-protecting agents, and mixtures thereof.

It is a matter of routine operations for a person skilled in the art to adjust the nature and amount of the additives present in the compositions in accordance with the present invention such that the advantageous properties of the composition used according to the present invention are not, or are not substantially, adversely affected by the envisaged addition.

According to a preferred embodiment, the invention relates to a solid anhydrous composition comprising:
a) from 15% to 40% by weight of triglyceride oil according to formula (I) chosen from caprylic/capric acid triglycerides, canola oil, or mixture thereof, relative to the total weight of the composition,
b) from 20% to 50% by weight of castor oil, relative to the total weight of the composition,
c) Bis-Behenyl/Isostearyl/Phytosteryl Dimer Dilinoleyl Dimer Dilinoleate, and
d) a wax chosen from sunflower wax, carnauba wax, or mixture thereof, Wherein a) caprylic/capric acid triglycerides, canola oil, or mixture thereof, and b) castor oil are present in the solid anhydrous composition in a weight ratio less than or equal to 1:1.

Although does not wish to be limited by any theory, it is believed that sunflower seed wax or carnauba wax would build up the crystal structure to support the oil phase while triglyceride oil according to formula (I) chosen from caprylic/capric acid triglycerides, canola oil, or mixture thereof, castor oil and Bis-Behenyl/Isostearyl/Phytosteryl Dimer Dilinoleyl Dimer Dilinoleate would give sufficient viscosity to hold up the oil phase together.

Galenic Form

The composition of the present invention is suitable to be used as a skin care, make up or cosmetic treatment product. More particularly, the composition of the present invention is in the form of make-up product such as lipstick and so on.

The composition according to the present invention may be prepared in a conventional manner.

The terms "between" and "ranging from" used herein should be understood as including the limits.

The present invention also relates to a process for caring for/making up keratin materials such as the skin and the lips, preferably the lips, by applying the solid anhydrous composition as described above to the keratin materials.

Unless defined otherwise, all technical and scientific terms used herein have the same meaning as commonly understand by one of ordinary skill in the art to which the present invention pertains.

The examples that follow are given as non-limiting illustrations of the present invention. The percentages are weight percentages.

EXAMPLES

Formulation Examples

The following compositions are prepared (the contents are expressed as weight percentages of active material, unless otherwise indicated):

| | content | |
|---|---|---|
| INCI name | Invention Example | Comparative Example |
| CANOLA OIL (Lipex Preact by the company AARHUSKARL SHAMN) ingredient a) according to the present invention | 16.27 | 16.27 |

-continued

| INCI name | content | |
|---|---|---|
| | Invention Example | Comparative Example |
| POLYGLYCERYL-2 TRIISOSTEARATE | 10 | 10 |
| CAPRYLIC/CAPRIC TRIGLYCERIDE (Wilfare Ster MCT from Wilmar) ingredient a) according to the present invention | 12.5 | 30 |
| RICINUS COMMUNIS (CASTOR) SEED OIL (Lipovol CO from Vantage Specialty Chemicals) ingredient b) according to the present invention | 37.5 | 20 |
| BIS-BEHENYL/ISOSTEARYL/ PHYTOSTERYL DIMER DILINOLEYL DIMER DILINOLEATE (Plandool G7 from Nippon Fine Chemical Co., Ltd.) ingredient c) according to the present invention | 8.5 | 8.5 |
| HELIANTHUS ANNUUS (SUNFLOWER) SEED WAX (Sunflower Wax from Koster Keunen) ingredient d) according to the present invention | 6.5 | 6.5 |
| COPERNICIA CERIFERA (CARNAUBA) WAX (Cerauba T1 Bio from Baerlocher) ingredient d) according to the present invention | 1.5 | 1.5 |
| RED 28 LAKE | 7.23 | 7.23 |

The weight ratio of the ingredient a) and b) as claimed in the Comparative example is 2.3:1, which is out of the scope of the present invention.

Protocol of Preparation

The above listed compositions were prepared following the steps of:

Mixing all the ingredients under 93° C., stirring the mixture at 300r/min by IKA Blender Euro—ST P CV S25 model until homogeneous;

Pouring the homogenized mixture into a lip stick mould at 93° C., leaving the mixture in the mould under 25° C. until solidation; and Demoulding the solid mixture from the lip stick mould.

Evaluation Example

Evaluation on the hardness, stability of the shape, and anti-sweating as well as usage effect such as spreadability, and homogeneous wear, non-sticky feeling after application of the composition according to invention and comparative examples are performed.

Hardness was evaluated according to the protocol described previously.

Stability of the shape was evaluated using crash test, by following steps:

Heating the composition to 38° C. for 24 hours; and

Applying the composition to the lips under the heated temperature.

Spreadability is evaluated by 5 experts by the following steps:

Repeatedly applying the composition three times on the same area of the forearm using the same force;

Weighing the weight loss of the composition;

Measuring the size of the area on the forearm where the composition is applied;

Calculating the weight loss per square centimetre; and

Finally, comments or scores were given by the experts on the above mentioned properties.

5: very good;
4: basically good;
3: acceptable;
2: slightly poor and not acceptable;
1: poor, not acceptable.

Anti-sweating was evaluated by 5 experts by the following steps:

Firstly, putting the compositions according to invention and comparative examples in the same room;

Then, raising the room temperature to above 35° C.;

Lastly, scores are given by the experts based on that whether the composition sweats.

5: the composition does not sweat at all;
4: the composition basically does not sweat;
3: the composition slightly sweats;
2: the composition sweats a lot;
1: the composition substantially sweats.

The non-sticky feeling and homogeneous wear after application were evaluated by 5 experts by the following steps:

Firstly, repeatedly applying the compositions according to invention and comparative examples, respectively, three times on the same area of the lips using the same force;

Then comments or scores are given by the experts on the above mentioned properties.

5: very good;
4: basically good;
3: acceptable;
2: slightly poor and not acceptable;
1: poor, not acceptable.

| Properties | Scores of the example | |
|---|---|---|
| | Invention Example | Comparative Example |
| Hardness | 5 | 4 |
| Stability of the shape | Stable over 10 stroke | Stable over 10 stroke |
| Spreadability | 5 | 5 |
| Homogeneous wear | 5 | 4 |
| Non-sticky feeling | 5 | 5 |
| Anti-sweating | 5 | 2 |

It is observed that the compositions according to invention example possesses good stability of shape, improved anti-sweating, and usage effect while the composition according to comparative example presents a sweating issue, which is not desired.

Based on the above listed evaluation results, the inventors discovered that the composition according to the present invention overcomes some technical issues existing in the prior arts, and provides a solid anhydrous composition with desired hardness and good usage.

The invention claimed is:

1. A solid anhydrous composition for caring for and/or making up keratin materials comprising, a) at least one triglyceride oil according to formula (I):

$$CH_2(OOCR_1)CH(OOCR_2)CH_2(OCR_3) \quad (I)$$

wherein $R_1$, $R_2$ and $R_3$ are independently chosen from $C_6$-$C_{30}$ alkyl and $C_6$-$C_{30}$ alkenyl;

b) at least one triglyceride oil according to formula (II):

$$CH_2(OOCR_1)CH(OOCR_2)CH_2(OOCR_3) \quad (II)$$

wherein $R_1$, $R_2$ and $R_3$ are independently chosen from $C_6$-$C_{30}$ alkyl and $C_6$-$C_{30}$ alkenyl, with the proviso that at least one of $R_1$, $R_2$ and $R_3$ is substituted with a hydroxyl;

c) at least one pasty compound selected from an ester of dimer dilinoleic acid and polyol(s) or an ester thereof, and
d) at least one wax;

wherein the triglyceride oil according to formula (I) and the triglyceride oil according to formula (II) are present in the solid anhydrous composition in a weight ratio less than or equal to 1:1.

2. The composition according to claim 1, further comprising an additional oil selected from nonvolatile hydrocarbon-based oil of plant origin selected from the group consisting of plant oils, nonvolatile oils of high molecular mass between 350 and 10 000 g/mol, and mixtures thereof.

3. The composition according to claim 1, wherein the wax is selected from the group consisting of hydrocarbon-based waxes of plant or animal origin, esters obtained by catalytic hydrogenation of animal or plant oils, and a mixture thereof.

4. The composition according to claim 1, wherein further comprising at least one dyestuff selected from water-soluble dyestuffs, water-insoluble dyestuffs, liposoluble dyestuffs, non-liposoluble dyestuffs, organic dyestuffs, mineral dyestuffs, materials with an optical effect, and mixtures thereof.

5. The composition according to claim 1, wherein, in formula (I), $R_1$, $R_2$ and $R_3$ are independently selected from $C_6$-$C_{20}$ alkyl and $C_6$-$C_{20}$ alkenyl.

6. The composition according to claim 1, wherein, in formula (II), $R_1$, $R_2$ and $R_3$ are independently selected from $C_6$-$C_{20}$ alkyl and $C_6$-$C_{20}$ alkenyl wherein at least one of $R_1$, $R_2$ and $R_3$ is substituted with a hydroxyl.

7. The composition according to claim 1, wherein the pasty compound is selected from an ester of dimer dilinoleic acid and polyol(s) or an ester thereof is chosen from the compound of formula (III):

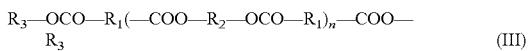

$$R_3\text{—OCO—}R_1(\text{—COO—}R_2\text{—OCO—}R_1)_n\text{—COO—}R_3 \quad (III)$$

wherein:
COR$_1$CO represents a dimer dilinoleate residue,
OR$_2$O represents a fatty alcohol dimer residue ranging from $C_{16}$ to $C_{68}$,
OR$_3$ represents a monoalcohol residue ranging from 4 to 40 carbon atoms, and
n is an integer ranging from 1 to 15.

8. The composition according to claim 1, wherein the pasty compound selected from an ester of dimer dilinoleic acid and polyol(s) or an ester thereof is selected from the compound of formula (IV):

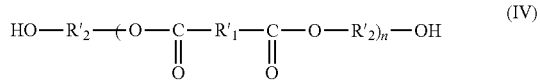

wherein:
n is an integer ranging from 1 to 15, —OCR'$_1$CO represents a dimer dilinoleate residue,
OR'$_2$O represents a diglyceryl residue of general formula (V) below:

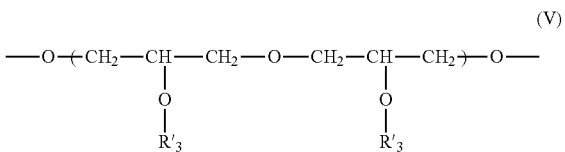

wherein:
R'$_3$ represents H or OR'$_3$ represents a fatty acid residue that may range from $C_8$ to $C_{34}$.

9. The composition according to claim 1, wherein the pasty compound selected from an ester of dimer dilinoleic acid and polyol(s) or an ester thereof is selected from the group consisting of esters having the following INCI nomenclature: polyglyceryl-2 isostearate dimer dilinoleate copolymer, bis-behenyl/isostearyl/phytosterol dimer dilinoleyl dimer dilinoleate, and mixtures thereof.

10. The composition according to claim 1, wherein the at least one triglyceride oil according to formula (I) is present in an amount ranging from 15% to 40% by weight relative to the total weight of the composition.

11. The composition according to claim 1, wherein the at least one triglyceride oil according to formula (II) is present in an amount ranging from 20% to 50% by weight relative to the total weight of the composition.

12. The composition according to claim 1, wherein the at least one chosen from an ester of dimer dilinoleic acid and polyol(s) or an ester thereof is present in an amount ranging from 5% to 15% by weight relative to the total weight of the composition.

13. The composition according to claim 1, wherein the at least one wax is present in an amount ranging from 5% to 15% by weight relative to the total weight of the composition.

14. The composition according to claim 1, wherein the weight ratio of the triglyceride oil according to formula (I) and triglyceride oil according to formula (II): the at least one pasty compound(s) selected from an ester of dimer dilinoleic acid and polyol(s) or an ester thereof ranges from 3:1 to 10:1.

15. A process for caring for and/or making up keratin materials, comprising: applying the composition according to claim 1 to the keratin materials.

* * * * *

UNITED STATES PATENT AND TRADEMARK OFFICE
CERTIFICATE OF CORRECTION

PATENT NO. : 11,185,484 B2
APPLICATION NO. : 16/649865
DATED : November 30, 2021
INVENTOR(S) : Yao It is certified that error appears in the above-identified patent and that said Letters Patent is hereby corrected as shown below:

In the Claims

Column 20, Claim 1, Line 57, delete "$CH_2(OOCR_1)CH(OOCR_2)CH_2(OCR_3)$" and insert -- $CH_2(OOCR_1)CH(OOCR_2)CH_2(OOCR_3)$ --.

Column 22, Claim 9, Line 24, delete "bis-behenyl/isostearyl/phytosterol" and insert -- bis-behenyl/isostearyl/phytosteryl --.

Signed and Sealed this
Twenty-fourth Day of May, 2022

Katherine Kelly Vidal
*Director of the United States Patent and Trademark Office*